(12) United States Patent
Johansson

(10) Patent No.: US 8,821,538 B2
(45) Date of Patent: Sep. 2, 2014

(54) IMPLANTABLE TISSUE STRUCTURE MODIFIERS AND METHODS FOR USING THE SAME

(76) Inventor: Peter Karl Johansson, Lafayette, CA (US)

(*) Notice: Subject to any disclaimer, the term of this patent is extended or adjusted under 35 U.S.C. 154(b) by 338 days.

(21) Appl. No.: 12/950,924

(22) Filed: Nov. 19, 2010

(65) Prior Publication Data

US 2011/0125169 A1 May 26, 2011

Related U.S. Application Data

(60) Provisional application No. 61/263,018, filed on Nov. 20, 2009, provisional application No. 61/302,367, filed on Feb. 8, 2010.

(51) Int. Cl.
| | |
|---|---|
| *A61B 17/00* | (2006.01) |
| *A61L 31/14* | (2006.01) |
| *A61M 25/00* | (2006.01) |
| *A61F 2/24* | (2006.01) |
| *A61M 25/09* | (2006.01) |
| *A61M 25/01* | (2006.01) |

(52) U.S. Cl.
CPC ............ *A61M 25/00* (2013.01); *C08L 2201/12* (2013.01); *A61L 31/14* (2013.01); *A61M 25/0108* (2013.01); *A61M 25/01* (2013.01); *A61F 2/2445* (2013.01); *A61L 2400/16* (2013.01); *A61M 25/09* (2013.01)
USPC ........... 606/221; 606/151; 606/215; 606/216; 606/219

(58) Field of Classification Search
USPC .......................................... 606/221; 411/468
See application file for complete search history.

(56) References Cited

U.S. PATENT DOCUMENTS

| | | | | |
|---|---|---|---|---|
| 3,939,828 A | * | 2/1976 | Mohr et al. | 606/916 |
| 4,396,139 A | * | 8/1983 | Hall et al. | 227/19 |
| 5,007,921 A | * | 4/1991 | Brown | 606/221 |
| 5,026,390 A | * | 6/1991 | Brown | 606/221 |
| 6,059,787 A | * | 5/2000 | Allen | 606/75 |
| 6,152,935 A | * | 11/2000 | Kammerer et al. | 606/144 |
| 6,273,903 B1 | * | 8/2001 | Wilk | 606/219 |
| 6,607,542 B1 | * | 8/2003 | Wild | 606/157 |
| 6,726,695 B2 | * | 4/2004 | Tong | 606/151 |
| 7,004,958 B2 | * | 2/2006 | Adams et al. | 606/219 |
| 2001/0003986 A1 | | 6/2001 | Cosgrove | |
| 2003/0045893 A1 | | 3/2003 | Ginn | |
| 2003/0074012 A1 | | 4/2003 | Nguyen et al. | |
| 2003/0178033 A1 | | 9/2003 | Cosgrove | |
| 2005/0080454 A1 | | 4/2005 | Drews et al. | |

(Continued)

FOREIGN PATENT DOCUMENTS

WO 9944534 9/1999

*Primary Examiner* — Melanie Tyson
*Assistant Examiner* — Todd J Scherbel
(74) *Attorney, Agent, or Firm* — Bret E. Field; Bozicevic, Field & Francis LLP

(57) ABSTRACT

Implantable tissue structure modification devices are provided. Aspects of the tissue structure modification devices include first and second tissue securers separated by a contraction region, wherein the device is configured to be implanted at a cardiac location and assume a first constrained length that is longer than a second relaxed length. Also provided are methods of using the devices for tissue structure modification, as well as delivery systems and kits that find use in the methods. The devices and methods of the invention find use in a variety of different applications, including valve (e.g., mitral valve) structure modification.

17 Claims, 11 Drawing Sheets

(56) References Cited

U.S. PATENT DOCUMENTS

| | | |
|---|---|---|
| 2005/0107871 A1* | 5/2005 | Realyvasquez et al. ..... 623/2.11 |
| 2006/0074484 A1 | 4/2006 | Huber |
| 2006/0089711 A1 | 4/2006 | Dolan |
| 2007/0049952 A1 | 3/2007 | Weiss |
| 2007/0073274 A1 | 3/2007 | Chin et al. |
| 2007/0093869 A1 | 4/2007 | Bloom et al. |
| 2007/0208297 A1 | 9/2007 | Ainsworth et al. |
| 2008/0183283 A1 | 7/2008 | Downing |
| 2010/0063506 A1* | 3/2010 | Fox et al. ................ 606/75 |
| 2010/0262041 A1 | 10/2010 | Von Malmborg |

* cited by examiner

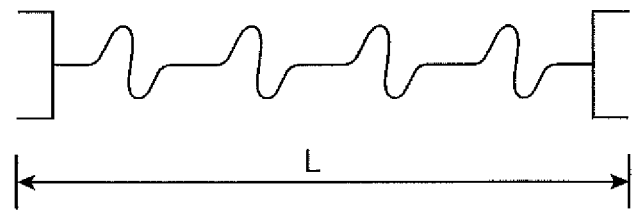
FIG. 3
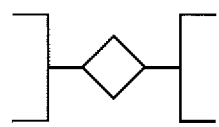          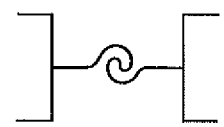
FIG. 4A     FIG. 4B     FIG. 4C
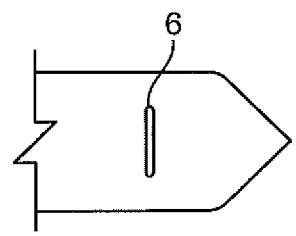
FIG. 5

IMPLANTABLE TISSUE STRUCTURE MODIFIERS AND METHODS FOR USING THE SAME

CROSS-REFERENCE TO RELATED APPLICATIONS

Pursuant to 35 U.S.C. §119 (e), this application claims priority to the filing date of the U.S. Provisional Patent Application Ser. No. 61/302,367 filed Feb. 8, 2010; and to the filing date of the U.S. Provisional Patent Application Ser. No. 61/263,018 filed Nov. 20, 2009; the disclosures of which applications are herein incorporated by reference.

INTRODUCTION

The mitral valve is a heart valve composed of two leaflets (anterior and posterior) demarcated by two commissures along an annular ring. The mitral valve separates the left atrium from the left ventricle, and functions as a regulator for the entrance of blood from the left atrium into the left ventricle. The valve opens during diastole to allow oxygenated blood to flow from the left atrium into the left ventricle. The mitral valve closes during systole (with the two leaflets coapting and forming a seal), while the aortic valve simultaneously opens, allowing blood to escape the constricting left ventricle. The valve leaflets of the mitral valve are attached distally by fibrous strands, called chordae tendineae, to papillary heart muscles in the cavity of the left ventricle. Normal and proper valve function of the mitral valve depends on the complex interactions of all these components, commonly referred to as the mitral valve apparatus.

Any disorder that weakens or damages the mitral valve leaflets or causes the left ventricle to become widened may lead to loss of leaflet coaptation and subsequent mitral regurgitation, a term used to describe an abnormal reverse-flow of oxygenated blood flow from the left ventricle to the left atrium. Over time, blood backs up into the atrium and lungs and the heart has to work harder to tolerate the loss due to regurgitation and continue to pump blood to the rest of the body. Mitral regurgitation may lead to congestive heart failure.

Traditional treatment of mitral regurgitation typically involves an open-heart surgical procedure to replace the valve or repair the widened ventricle to return the mitral valve to efficient functionality. Valve repair procedures usually involve annuloplasty, which is a set of techniques designed to restore the valve annulus shape and strengthen the annulus. Conventional annuloplasty surgery generally requires a large incision into a patient's thorax, and sometimes an incision through a patient's sternum. These open-heart, open-chest procedures routinely involve placing the patient on a heart-lung bypass machine for long periods of time so that the patient's heart and lungs can be stopped to allow for surgical repair. In addition, valve repair and replacement is typically technically challenging and requires a substantial incision through a heart wall to access the valve. Most patients with mitral regurgitation are not even considered candidates for heart valve surgery because of the high risk involved.

SUMMARY

Implantable tissue structure modification devices are provided. Aspects of the tissue structure modification devices include first and second tissue securers separated by a contraction region, wherein the device is configured to be implanted at a cardiac location and assume a first constrained length that is longer than a second relaxed length. Also provided are methods of using the devices for tissue structure modification, as well as delivery systems and kits that find use in the methods. The devices and methods of the invention find use in a variety of different applications, including valve (e.g., mitral valve) structure modification.

BRIEF DESCRIPTION OF THE DRAWINGS

FIG. 3 is a schematic of a unibody implant according to an embodiment of the invention showing repeating geometric patterns, where the implant is shown in a low energy state.

FIG. 4 provides schematics of unibody implants according to various embodiments of the invention, where each of the implants depicts an alternative geometric pattern of the contraction region in a low energy state.

FIG. 5 is a detailed view of a tissue securer in the form of a hook, according to an embodiment of the invention.

FIG. 9b is a perspective illustration of a portion of the flat pattern design shown in FIG. 9a. In FIG. 9b, the tissue grabber or hook is shown in a retracted state, held in place by the control wire and delivery catheter (not shown).

DETAILED DESCRIPTION

Figure 1:
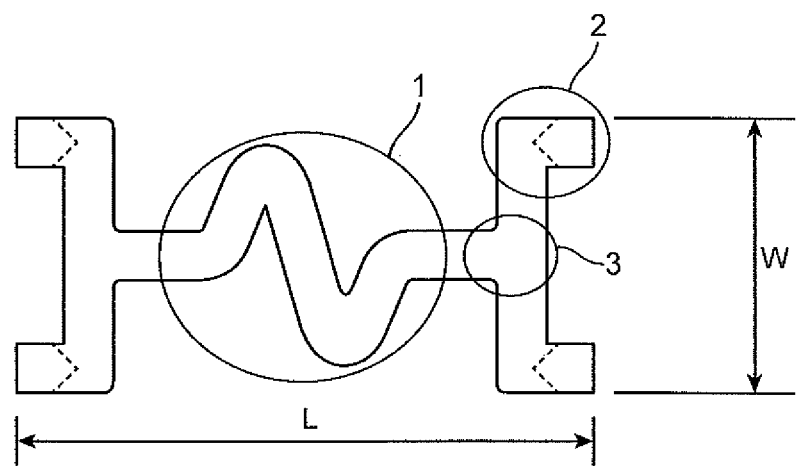
FIG. 1 is a top plan view of an implantable tissue structure modification device (i.e., a unibody implant) according to an embodiment of the invention, where the unibody implant is shown in a low energy state.

Implantable tissue structure modification devices are provided. Aspects of the tissue structure modification devices include first and second tissue securers separated by a contraction region, wherein the device is configured to be implanted at a cardiac location and assume a first constrained length that is longer than a second relaxed length. Also provided are methods of using the devices for tissue structure modification, as well as delivery systems and kits that find use in the methods. The devices and methods of the invention find use in a variety of different applications, including valve (e.g., mitral valve) structure modification.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of embodiments of the invention in greater detail, aspects of the devices and systems of various embodiments are reviewed first in greater detail, followed by a discussion of methods and kits according to certain embodiments of the invention.

Implantable Tissue Structure Modification Devices and Deployment Systems Including the Same As summarized above, aspects of the invention include implantable tissue structure modification devices. As the devices are implantable, they are dimensioned to be placed inside of a human body, and maintained therein for significant periods of time without adversely impacting living standards. In some instances, the implantable devices are dimensioned to be implanted inside of an organ, e.g., heart. Accordingly, in some instances the devices are dimensioned and configured to be implanted at a cardiac location, e.g., an internal cardiac location, such as a ventricle wall location, e.g., a mitral valve ventricle wall location. In some instances, the tissue structure modification devices have a longest dimension ranging from 1 to 12 inches, such as 2 to 9 inches and including 4 to 6 inches.

As devices of the invention are implantable, they are fabricated from a material or combination of materials that are suitable for being maintained in a human body for extended periods of time, e.g., (e.g., 1 week or longer, such as 1 month or longer, including 6 months or long, e.g., 1 year or longer, including 2 years or longer). Of interest in some embodiments are superelastic, e.g., Nitinol, etc. Superelastic materials of interest are those in which no heating is necessary to cause the undeformed shape to recover. Furthermore, Superelastic materials exhibit enormous elasticity, some 10-30 times that of ordinary metal.

Aspects of embodiments of the device include first and second tissue securers separated by a contraction region. The phrase "tissue securer" refers to any structure that is configured to stably associate the device with a defined tissue location for extended periods of time (e.g., 1 week or longer, such as 1 month or longer, including 6 months or long, e.g., 1 year or longer, including 2 years or longer) under physiological conditions, e.g., beating heart conditions. Tissue securers present on devices of the invention may have any convenient configuration, where configurations of interest include, but are not limited to: hooks, tines, springs, screws, anchors, etc., where the tissue securers may include one or more barbs, as desired. Devices of embodiments of the invention may have two or more tissue securers, with at least first and second tissue securers associated with first and second regions flanking a contraction region such that upon assumption of the relaxed state of the device, the tissue locations to which the tissue securers are stably associated move relative to each other in a desired manner sufficient to achieve the desired tissue structure modification. A given device may have more than two tissue securers located at various locations on the device, including first and second ends of the device, middle regions of device, etc. As such, a given device may include third and fourth tissue securers separated by a contraction region. Furthermore, a given device may include fifth and sixth tissue securers associated with a contraction region. The particular orientations of the given tissue securers of the device may vary as desired in order to stably associate the device with tissue upon deployment and achieve the desired tissue structure modification upon relaxation of the device following implantation.

As mentioned above, the device includes one or more contraction regions, where a contraction region is a region configured to assume a first constrained configuration and a second relaxed configuration. A given contraction region may include one or more curvilinear or linear portions, as desired. The length of the contraction region in the relaxed state may vary, ranging in some instances from 0.1 to 2 inches, such as 0.1 to 1 inch and including 0.1 to 0.5 inches. Likewise, the length of the contraction region in the constrained state may also vary, ranging in some instances from 0.5 to 4 inches such as 0.5 to 3 inches, and including 0.5 to 2 inches.

The devices can also have markers visible in ambient light as well as by fluoroscopy, ultrasound, computed tomography, magnetic resonance imaging, etc., which can indicate the location of the device on the delivery catheter or in a body, the location of tissue securers, and/or the location of contraction regions of the device. Markers can be used not only for location of the device or portions of the device, but can be used to indicate whether or not a tissue securer (e.g., hook) or contraction region of the device is fully deployed, e.g., in a fully relaxed state.

Devices according to embodiments of the invention are configured to be implanted at a cardiac location and assume a first constrained length that is longer than a second relaxed length. In some instances, the first constrained length is at least about 20% longer than the second relaxed length, such as at least about 30% longer than the second relaxed length, including at least about 40% or longer than the second relaxed length. In some instances, the first constrained length exceeds the second, relaxed length by 1 inch or more, such as by 2 inches or more, including 3 inches or more. In the second, relaxed configuration, the implant may assume an arced configuration in the relaxed state, where the radius of curvature of the arced implant may vary, ranging in some instances from 2 to 6 inches, such as 2 to 4 inches and including 2 to 3 inches. In some instances, the contraction region is structured to assume a linear constrained configuration and a curvilinear relaxed configuration.

Implantable tissue structure modification devices may be implanted using any convenient protocol. In some instances, the devices are configured to be associated in a constrained configuration with a minimally invasive deployment device, e.g., for minimally invasive implantation protocols. While minimally invasive deployment devices may vary, in some instances the devices are catheter devices that include one or more passageways or lumens, where the one or more passageways are configured to be associated with a tissue securer of the device prior to implantation. Wires or analogous releasing mechanisms may be employed to dissociate the implant from the deployment device during implantation.

Turning now to the figures, an implant according to one embodiment of the present invention is shown in FIG. 1. In FIG. 1, the structure is fabricated from a sheet of implantable material, the sheet thickness ranging from 0.003 inches to 0.030 inches. The structure has an overall length, L, ranging from 1 inch to 5 inches and width, W, ranging from 0.1 inches to 0.75 inches. The structure shown in FIG. 1 has one central contraction section or region, multiple tissue securers in the form of hook or tine portions, and a central portion for each hook or tine. The functions of each of these components are described in greater detail below.

Figure 2:
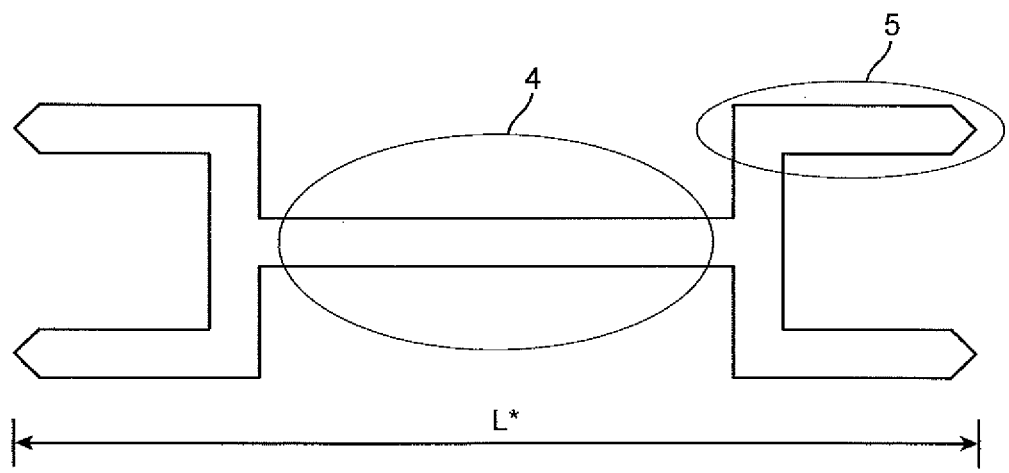
FIG. 2 is a top plan view of the unibody implant shown in FIG. 1, wherein the implant is depicted in a high energy state.

The implant of FIG. 1 is shown again in FIG. 2 with an extended contraction section and extended hooks or tines. The effect of extending the implant is a change in structure length of the implant from L to L*. The implant of FIG. 1 is shown in a relatively low energy state, while the implant of FIG. 2 is shown in a positive potential energy state. The two states will be referred subsequently as (1) Delivery and (2) Implantation. The two states can be achieved by use of material superelasticity (e.g. Nitinol®) and/or elastic or plastic deformation of a crystalline solid (e.g. Stainless Steel, Elgiloy®, etc.). The structure shown in FIG. 1, and of a selected material, may be readily fabricated using currently available technologies, such as laser-cutting, electrical discharge machining, etc., as desired.

FIG. 3 represents a schematic drawing of an alternative embodiment of the implant according to an embodiment of the present invention. The overall implant length, L, is shown in FIG. 3; the single contraction section of FIG. 1 is a subset of FIG. 3, and is repeated 4 times. This repeating pattern allows one to design a target overall length change from L* (each contraction section extended (not shown)) to L (each contraction section contracted to the lowest energy state), shown in FIG. 3.

The contraction sections shown in FIGS. 1, 2, and 3 are but one possible configuration. Other alternative contraction sections are illustrated schematically in FIGS. 4A-C (e.g., wherein the contraction section in the relaxed configuration is in the shape of a diamond, a semi-circle, or a "wave-form"). Other shapes, including but not limited to a circle, an oval, arcs or curves of varying radius, a spiral shape, an angled or zigzag shape, are possible. In some embodiments, the contraction section is a continuous single piece, as shown in FIGS. 4B and 4C. In other embodiments, as shown in FIG. 4A, for example, at least a portion of the contraction section can be formed of two pieces, e.g., that form a diamond shape when in the relaxed configuration. In FIG. 4, contraction sections are shown in the Implantation state.

Figure 6:
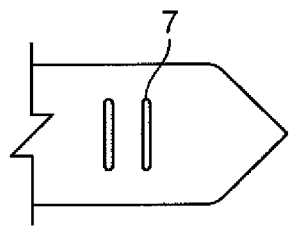
FIG. 6 is a detailed view of a tissue securer in the form of a hook, according to an embodiment of the invention.

The hooks or tines of FIG. 1 are shown in detail in FIG. 5 and FIG. 6. The hooks or tines are shown with holes or slots designed to temporarily capture retention wires (disclosed in greater below). When released, the hooks or tines capture and secure to local organ cavity tissue.

Figure 7:
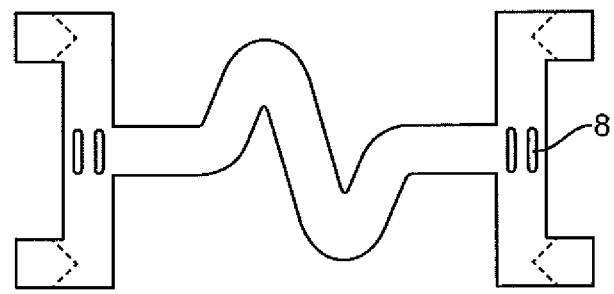
FIG. 7 is a top plan view of a unibody implant showing slots or holes at the central portions of the device, according to one embodiment of the invention.

The holes or slots of FIG. 5 and FIG. 6 may also be located in the central portions of the hooks or tines, to capture temporarily retention wires (disclosed below), as illustrated in FIG. 7. When captured by the retention wires, the implant is restrained in length, L*. When released, the implant recovers to length L.

Figure 8:
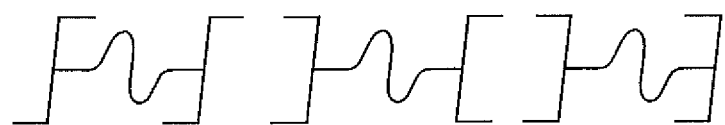
FIG. 8 provides schematic views of unibody implant configurations according to various embodiments of the invention, where alternative hook and tine configurations are depicted.
Figure 8:
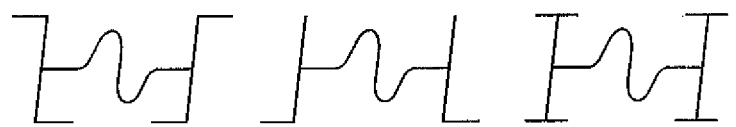

In some instances, pluralities of hooks or tines are present on the implant portion of the tissue structure modification device in order to secure the device to the tissue of an organ cavity. Where desired, different orientations of hooks or tines are present. Shown schematically in FIG. 8 is a variety of possible permutations of the implant of FIG. 1, with different hook or tine configurations. In reference to FIG. 8, only one contraction section design is shown. Alternative contraction sections as illustrated in FIGS. 3 and 4 may be used in combination with alternative hook or tine configurations of FIG. 8, as desired.

Figure 9A:
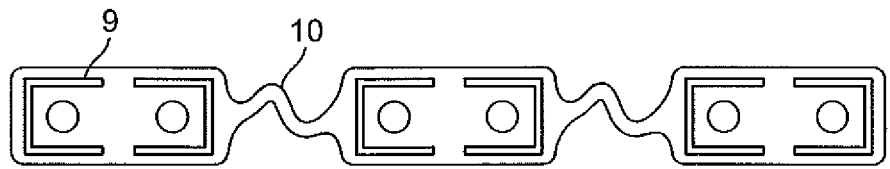
FIG. 9a is a top plan view of an alternative embodiment of the invention. The flat-pattern representation shows how the device would be portrayed in two dimensions for the purpose of manufacturing (e.g. laser-cutting).
Figure 9B:
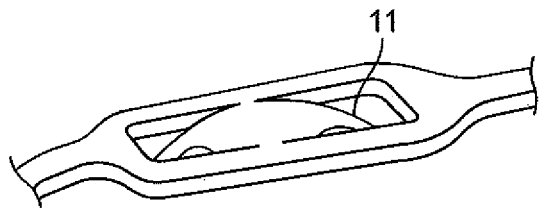
Figure 9C:
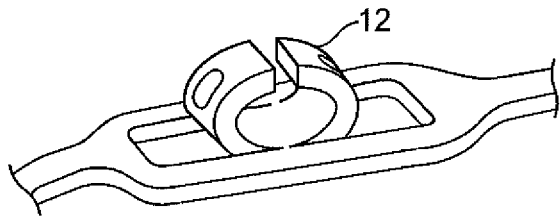
FIG. 9c is a perspective illustration of the same portion of the implant as shown in FIG. 9b, with the tissue grabber or hook shown in a released state. The action of two opposing tissue grabbers is intended to provide an ideal tissue grasping device to secure the trabeculae carneae columns of the heart chamber wall.

FIG. 9 shows a unibody implant according to one embodiment of the invention during delivery to a circumferential portion of an organ cavity and prior to implantation. By "unibody" is meant that the implant is constructed as a single structure, i.e., the implant is made of a single piece of material, such as nitinol, In some instances, the implant can be constructed of more than one piece of material. The implant is shown constrained in overall length, L*, and overall radius, R* (i.e., the radius of the target organ cavity prior to implantation of the device) in 9B, using means disclosed in FIG. 5, FIG. 6, and FIG. 7. In FIG. 9C, the implant is shown in a deployed position.

Figure 10:
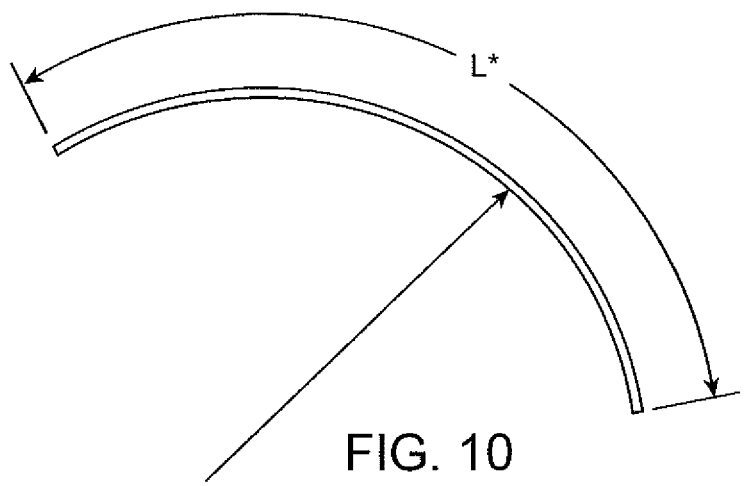
FIG. 10 is a top plan schematic view of a unibody implant length shown during delivery and prior to implantation, according to an embodiment of the invention.
Figure 11:
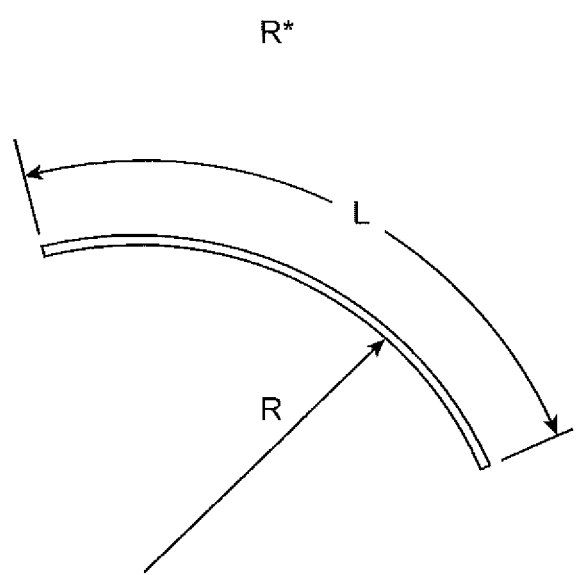
FIG. 11 is a top plan schematic view of the unibody implant length of the device shown in FIG. 9, where the device is shown following complete implantation of the device.

FIG. 10 is a top plan schematic view of the unibody implant of FIG. 9 following delivery to a circumferential portion of an organ cavity (e.g. as indicated in FIG. 9). In FIG. 11, the implant length is shown following complete release and implantation. The implant is shown in its recovered, reduced overall arc length, L, and reduced radius, R (i.e., the radius of the target organ cavity following implantation of the present invention).

Figure 12:
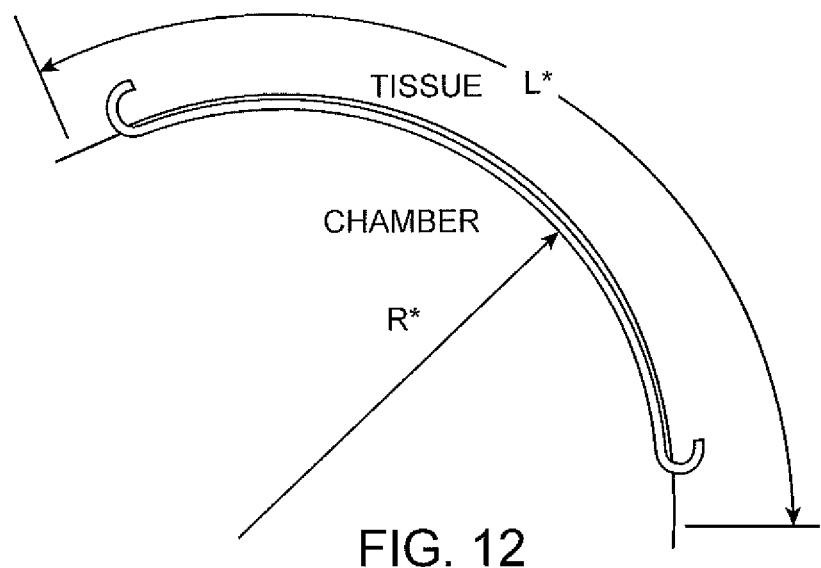
FIG. 12 is a top plan schematic view of a unibody device according to an embodiment of the invention, showing the implant length and tissue anchoring during delivery and prior to final implantation of the device.

FIG. 12 shows a unibody implant according to one embodiment of the invention during delivery to a circumferential portion of an organ cavity and prior to complete implantation. In FIG. 12, the implant is shown constrained between the hook and tine portions using means disclosed in FIG. 7, but the most proximal and distal hooks or tines have been released, grasping local tissue of the target cavity.

Figure 13:
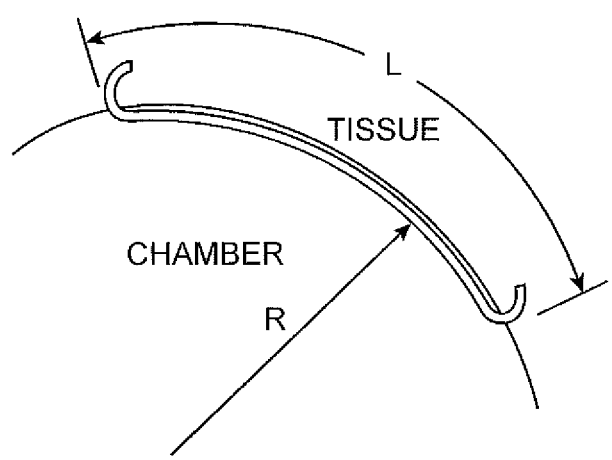
FIG. 13 is a top plan schematic view of the unibody device shown in FIG. 11, where the implant length and tissue anchoring following complete implantation of the device are depicted.

FIG. 13 is a top plan schematic view of the unibody implant shown in FIG. 11 of the present invention following delivery to a circumferential portion of an organ cavity (e.g. as indicated in FIG. 9). As shown in FIG. 13, the implant arc length, L, is illustrated following complete release and implantation. The implant is shown in its recovered, contracted shape as indicated in FIG. 1, shortened overall arc length, L, and reduced overall radius, R, and with released hooks or tines of FIG. 5 and FIG. 6. The effect of this implant delivery is a reshaped tissue and chamber of the organ cavity.

Figure 14:
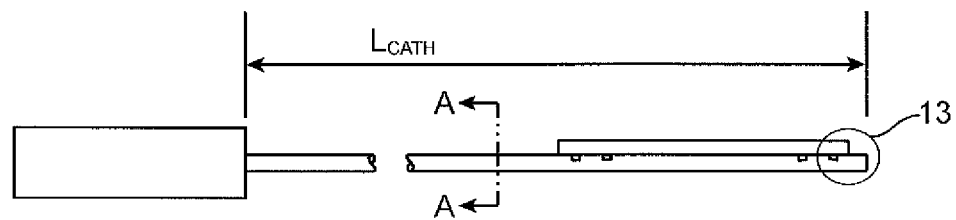
FIG. 14 is top plan view of a delivery device and implant assembly according to an embodiment of the invention.

In the top plan view of the catheter and implant assembly of FIG. 14 of the present invention, the implant and hooks and tines of the implant are reliably secured to the catheter using the holes or slots of FIG. 5, FIG. 6, and FIG. 7. The release wires, which run continuously from the point of engagement with the implant, as shown in FIG. 5, FIG. 6, and FIG. 7, to the handle, are manually controlled by means of control knobs or similar means of a handle (disclosed further below). As is customary, the portion of the catheter farthest away from the handle and user is referred to as "distal," while the portion of the catheter closest to the handle and user is referred to as "proximal." The catheter, not including the handle, is of suitable length (indicated as $L_{CATH}$ in FIG. 14) to access the target organ cavity (e.g. left ventricle) from a relatively remote access point (e.g. femoral artery). The purpose of restraining the implant prior to delivery is to control its primary function (i.e. altering an organ cavity shape) while maintaining a small profile, provide for access and prevention of trauma during passage through lumens (e.g. arteries).

Figure 15:
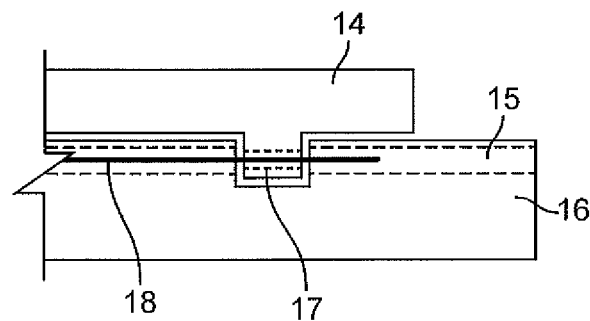
FIG. 15 is a detailed view of the implant retention feature of the delivery device shown in FIG. 14 prior to a hook release.

In FIG. 15, the detailed view of a portion of the catheter and implant assembly of FIG. 14 shows a control wire of the catheter device, passing through a slot or hole of a hook or tine of FIG. 5 or FIG. 6 of the implant of FIG. 1. The wire, ranging in diameter from 0.005 inches to 0.03 inches, primarily resides in a lumen of the catheter of FIG. 15. A local section of the catheter exposes the wire intermittently. This local section may be provided using any convenient protocol, e.g., by cutting and removing material using any convenient method. It is in this region that the control wire, or deployment wire, passes through the hole or slot of FIG. 5 or FIG. 6 and then returns to the continuing lumen of the catheter. The wire may be of a material having any suitable section modulus and shear resistance so as to effectively restrain the hook or tine via the hole or slot. The catheter may be any strength suitable to withstand the forces imparted by the constrained hook or tine and subsequently by the control wire and implant.

Figure 16:
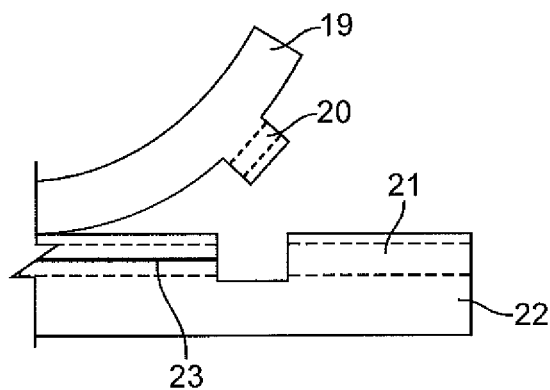
FIG. 16 is a detailed view of the implant retention feature of the device shown in FIGS. 14 and 15 following release of a hook and subsequent movement from delivery state to implantation state.

In FIG. 16, the detailed view of a portion of the catheter and implant assembly of FIG. 14 shows a control wire of the catheter device, described in its delivery state in FIG. 15, as having been retracted (i.e. moved proximally), releasing its capture of the hole or slot of the hook or tine. Being no longer constrained, the hook or tine moves to its lower energy position, capturing and securing to the local tissue, as illustrated in FIG. 12 and FIG. 13.

Figure 17:
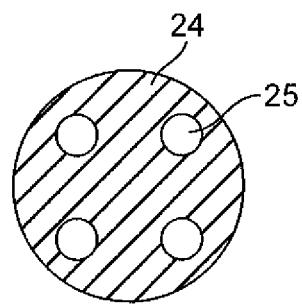
FIGS. 17, 18 and 19 are cross-sectional views taken along the line A-A of FIG. 14 of the delivery device, according to different embodiments of the device.
Figure 18:
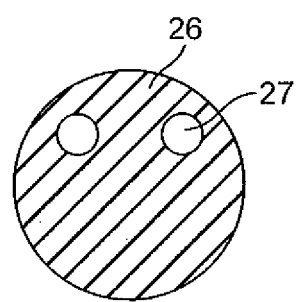
Figure 19:
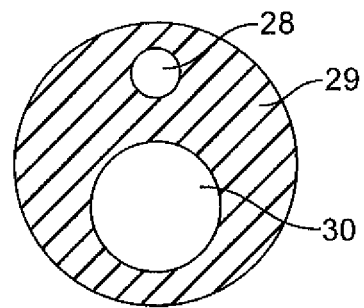

FIG. 17, FIG. 18, and FIG. 19 all show cross-sectional views taken along line A-A of FIG. 14 of the present invention. Each view shown is an alternative embodiment for different numbers of control wires to release the implant hooks or tines and central portions. Individual, dedicated control wires, shown in lumens of a continuous extrusion, could be used for each hook or tine, and for each central portion, or one, single control wire could be used to release all portions of the implant. FIG. 19 also shows a lumen available for use of a guidewire, a guidance device typically used to advance interventional devices, such as catheters.

Figure 20:
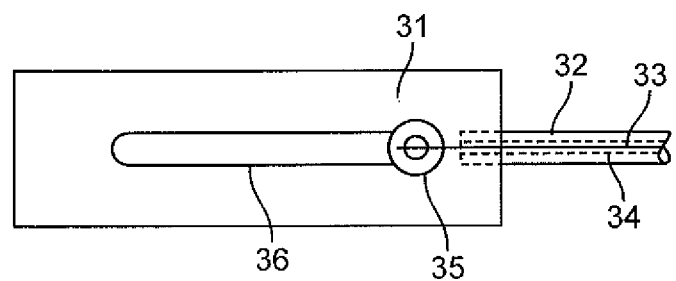
FIG. 20 is a detailed view of the user control handle of the delivery device shown in FIG. 14.

The user control handle of FIG. 14 of the present invention is shown in detail view in FIG. 20. Control surfaces (e.g. knobs or sliders) of the control handle are secured to the proximal end of the control wires of FIG. 16 using common means (e.g. adhesive, crimping, set screws, etc.). Proximal movement of each dedicated control surface within the provided slot in turn translates to proximal movement of the control wire within the catheter lumen, and directly to release of the implant hook or tine and central portions per FIG. 16. These are but some of the many possible methods for translating user input (e.g. pushing, pulling, turning) into the desired linear motion of the control wire; any convenient method may be employed. In some instances, some or all of the release mechanisms for the secured control wires can be automated or semi-automated (e.g., can operate by pushing a button, or operating a switch) such that the control wire can automatically retract a specific distance sufficient to deploy a tissue securer, for example. In other instances, the control handle can include combinations of manual and automatic methods for controlling deployment of the tissue securers or other portions of the device.

Figure 21:
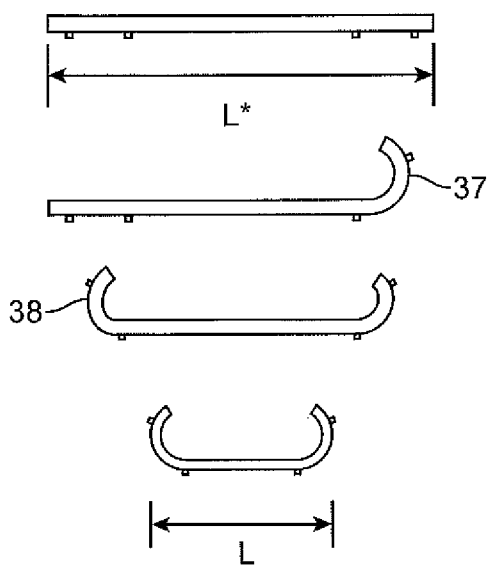
FIG. 21 provides a series of images illustrating a sequence of releasing a unibody implant of FIG. 1 from the delivery device of FIG. 14 during an implantation procedure according to an embodiment of the invention.

In FIG. 21, a series of images illustrate a simple, linear sequence of releasing the unibody implant of FIG. 1 from the catheter of FIG. 14. In FIG. 21, the catheter is not shown. Also in FIG. 21, the shape of the implant is shown with infinite radius, R, to simplify the illustration of tissue anchoring and length change; a more appropriate radius, suitable to the organ cavity shape, would be desirable. In the first image of FIG. 21, the implant is shown in its fully extended and constrained position. In the second image of FIG. 21, the first, most distal hook or tine is released from the catheter using the method shown in FIG. 16 and self-secures to the local tissue of the organ cavity wall. In the third image of FIG. 21, the proximal hook or tine is released from the catheter using the method shown in FIG. 16 and self-secures to the local tissue of the organ cavity wall. In the fourth image of FIG. 21, the distal and proximal contraction sections are released from the catheter using means identical to those shown in FIG. 16, allowing the implant to recover to its reduced length L and reduced radius R, the effect of which is a reshaped tissue of the organ cavity, as illustrated in FIG. 13.

Figure 22:
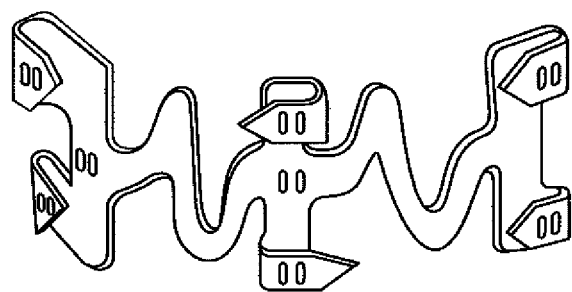
FIG. 22 is a perspective view of an embodiment of a unibody implant according to the invention.

A perspective view of another embodiment of the unibody implant of an embodiment of the present invention is shown in FIG. 22 in the deployed, low energy state. Two contraction sections are shown, with a total of six hooks or tines. This embodiment has slots for controlled release of the hooks or tines and of the contraction sections. The shape of the unibody implant is of a planar arc, with prominent hooks or tines to secure to the tissue of an organ cavity.

Figure 23:
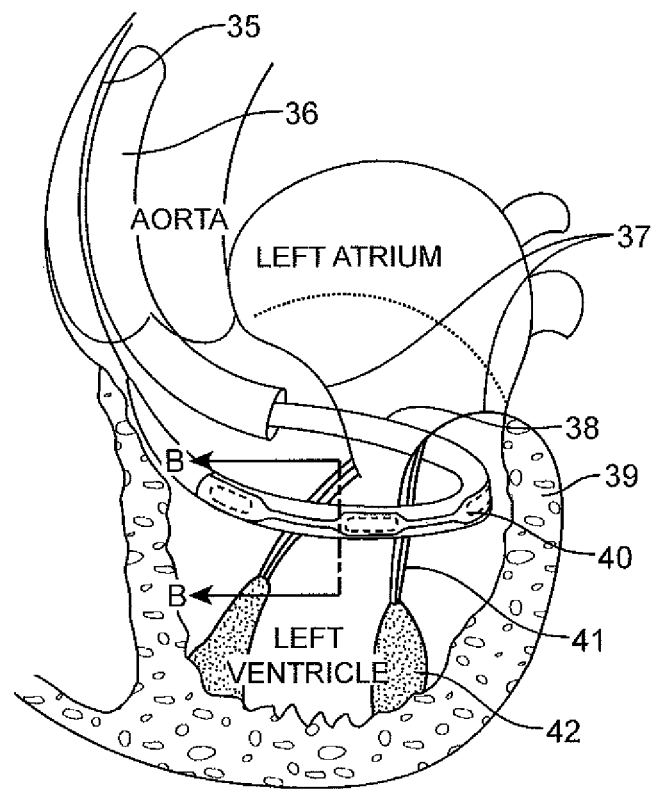
FIG. 23 is a perspective illustration of a human heart with a unibody implant in the undeployed state, secured to the distal portion of a catheter, positioned in the left ventricle

A simple illustration of the left chambers of a human heart is shown in FIG. 23, with the left atrium, left ventricle, mitral valve leaflets, annulus, and papillary muscles identified. For illustration purposes, a portion of the left ventricle has been removed, revealing the position and orientation of the distal portion of a delivery device and implant assembly according to an embodiment of the present invention.

Figure 24:
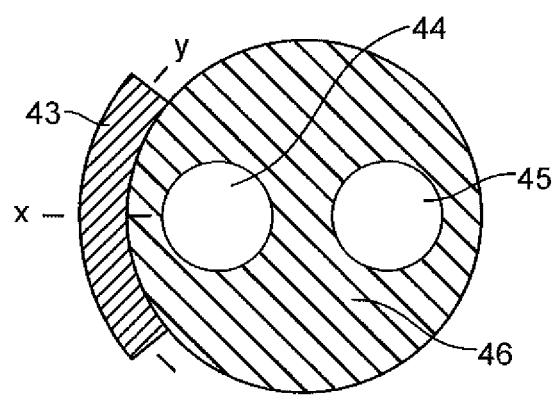
FIG. 24 is a cross-sectional view taken along the line B-B of the implant and catheter of FIG. 23.

FIG. 24 shows a cross-sectional view taken along line B-B of FIG. 23 of a portion of the present invention. This view shows the desired orientation of the implant and catheter relative to the left ventricular chamber wall. Indicated in FIG. 24 are the second moment of inertia axes of the implant, properties of cross-section dimensions that predict bending behavior. Theoretical calculations of second moment of inertia are well documented and utilized by those skilled in the art. For the cross-sectional area shown, the second moment of inertia for the x-axis of the implant is significantly greater than the second moment of inertia for the y-axis, in some instances by a magnitude of 5 or more, 10 or more, 20 or more, 50 or more, etc. This indicates a property of the implant to be more flexible in bending about the y-axis than in bending about the x-axis. During introduction and advancement of the implant and catheter into the left ventricle, the bias in flexibility of the implant due to the differential in second moment of inertias will result in a tendency of the implant to orient in a desired direction, i.e. with the hooks or tines facing away from the central axis of the ventricular chamber, toward the ventricular wall. FIG. 24 also shows the lumen of the catheter available for use of a guidewire and lumen of the catheter for use of the control wire.

The catheters and wires used in positioning and deployment of the implantable device, e.g., guide catheters and delivery catheters, guidewires and control wires, can in some embodiments have markings to assist in positioning or deployment of the implantable device, or to measure the tissue location of interest. For example, a catheter can have markers visible by fluoroscopy, ultrasound, computed tomography, etc., which can indicate the location of the implantable device on the delivery catheter, or can indicate the sections of the delivery catheter where the control wire is exposed (e.g., as shown in FIG. 15). In another example, a guidewire or control wire used with the subject device can have markers to indicate the end of the wire, e.g., such that retraction of the distal end of a control wire can be clearly seen with respect to the section of the delivery catheter where the control wire passes through the hole or slot of FIG. 5 or FIG. 6.

Methods

The subject devices find use in methods of tissue restructuring, where the structure (i.e., physical configuration) of a tissue region is modified in a desirable manner. In certain instances, the subject devices and methods are employed to modify the structure of an organ location, such as a cardiac location, e.g., a cardiac valve location, such as a mitral valve. The subject devices therefore find use in methods of enhancing the function of a valve, such as a mitral valve, where enhancing the function means improving the operation of valve, such that the valve works in a manner that is more analogous to that of a valve in a healthy individual. The subject devices can be used in an open surgical procedure, a minimally invasive surgical procedure, an endovascular procedure, or other interventional procedure. Enhancement of valve function may be determined using any convenient measure or set of measures, including those described below in connection with diagnosis of the mitral valve regurgitation. The subject methods also include the step of diagnosing a patient in need of cardiac valve repair, e.g., mitral valve repair.

The signs and symptoms associated with mitral regurgitation can include symptoms of decompensated congestive heart failure (i.e.: shortness of breath, pulmonary edema, orthopnea, paroxysmal nocturnal dyspnea), as well as symptoms of low cardiac output (i.e., decreased exercise tolerance). Cardiovascular collapse with shock (cardiogenic shock) may be seen in individuals with acute mitral regurgitation due to papillary muscle rupture or rupture of a chorda tendinea. Individuals with chronic compensated mitral regurgitation may be asymptomatic, with a normal exercise tolerance and no evidence of heart failure. These individuals however may be sensitive to small shifts in their intravascular volume status, and are prone to develop volume overload (congestive heart failure).

Findings on clinical examination depend of the severity and duration of mitral regurgitation. The mitral component of the first heart sound is usually soft and is followed by a pansystolic murmur which is high pitched and may radiate to the axilla. Patients may also have a third heart sound. Patients with mitral valve prolapse often have a mid-to-late systolic click and a late systolic murmur.

Diagnostic tests include an electrocardiogram (EKG), which may show evidence of left atrial enlargement and left ventricular hypertrophy. Atrial fibrillation may also be noted on the EKG in individuals with chronic mitral regurgitation. The quantification of mitral regurgitation usually employs imaging studies such as echocardiography or magnetic resonance angiography of the heart. The chest x-ray in patients with chronic mitral regurgitation is characterized by enlargement of the left atrium and the left ventricle. The pulmonary vascular markings are typically normal, since pulmonary venous pressures are usually not significantly elevated. An echocardiogram, or ultrasound, is commonly used to confirm the diagnosis of mitral regurgitation. Color doppler flow on the transthoracic echocardiogram (TTE) will reveal a jet of blood flowing from the left ventricle into the left atrium during ventricular systole. Because of the difficulty in getting accurate images of the left atrium and the pulmonary veins on the transthoracic echocardiogram, a transesophageal echocardiogram (TEE) may be necessary to determine the severity of the mitral regurgitation in some cases. The severity of mitral regurgitation can be quantified by the percentage of the left ventricular stroke volume that regurgitates into the left atrium (the regurgitant fraction). Other methods that can be used to assess the regurgitant fraction in mitral regurgitation include cardiac catheterization, fast CT scan, and cardiac MRI.

Indications for surgery for chronic mitral regurgitation include signs of left ventricular dysfunction. These include an ejection fraction of less than 60 percent and a left ventricular end systolic dimension (LVESD) of greater than 45 mm.

Methods for modifying a tissue location in a subject can include positioning an implantable tissue structure modification device of the subject invention in a first constrained configuration at a tissue location, e.g., a ventricle. The implantable device can be introduced into a subject using a minimally invasive deployment device (e.g., a catheter), with one or more access sheaths, catheters and guidewires suitable for vascular access as is known by those of ordinary skill in the art.

In some embodiments, measurements of the tissue region of interest, e.g., region of the left ventricular wall proximate to the mitral valve, can be made using markers on a guidewire or catheter under imaging guidance, to determine the appropriate size of the device. When the device size has been selected, the guidewire and/or guide catheter with the preloaded implantable device can be advanced to the region of interest, such as the left ventricle, under fluoroscopic guidance. The guidewire and delivery catheter can be advanced from the aorta into the left ventricle, passing behind the chordae (as shown in FIG. 23), to position the delivery catheter in a roughly circular configuration just inferior to the position of the mitral valve.

Once the delivery catheter containing the device (in the constrained configuration) is in position, the device can be deployed by reducing the constraining force from the device in a manner sufficient for the device to assume a second relaxed configuration to engage tissue and modify the tissue location. The catheter can comprise a deployment wire that associates the implantable device to the deployment device in the first constrained configuration. The method comprises moving the deployment wire in a manner sufficient for the implantable device to dissociate from the deployment device and assume the second relaxed configuration. For example, the operator can deploy the device by operation of the control surfaces (e.g. knobs or sliders) of the control handle, which are secured to the proximal end of the control wires. At least a first and second tissue securer and/or and central portion between tissue securers (per FIGS. 6 and 7) which are either end of a contraction section can be deployed, which secures the device to the local tissue. The intervening contraction section can then be released from the delivery catheter using means identical to those shown in FIG. 16, allowing the implant to recover to its reduced length L and reduced radius R, the effect of which is a reshaped tissue of the organ cavity, as illustrated in FIG. 13.

The steps of deploying the device can be repeated as necessary, and in any suitable order. For example, as shown in FIG. 22, the most distal hooks can be released from the catheter and secured to tissue, followed by release of the middle hooks. The contraction section between the middle and distal hooks can then be released or deployed to its relaxed, or shortened length. The proximal hooks can then be released, followed by release of the contraction section between the middle and proximal hooks, etc.

Following deployment of the device, the modified tissue location can be assessed. For example, measurement of the organ dimensions can be made by imaging or by measurement of markers on a catheter or guidewire, or evaluation of the tissue location can include a functional assessment (e.g., evaluation of the degree of mitral regurgitation). In some embodiments, more than one implantable tissue modification structure may be implanted in a tissue location. For example, if a single device is deployed, and the anatomical or functional result is less than optimal (e.g., if a subject continues to have significant mitral regurgitation), a second device can be deployed in a suitable location in proximity to the first device, such that the combination of implanted devices results in sufficient modification of the tissue location such that the subject is treated for a condition (e.g., enhancing the function of a valve, such that the valve works in a manner that is more analogous to that of a valve in a healthy individual) In some embodiments, tissue modification with the implantable device will result in improved coaptation of the mitral valve leaflets, with reduction in mitral valve regurgitation.

The description of embodiments of the present invention is provided herein in certain instances with reference to a subject or patient. As used herein, the terms "subject" and "patient" refer to a living entity such as an animal. In certain embodiments, the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects, e.g., patients, are humans.

Systems and Kits

Also provided are kits that at least include the subject implantable devices, e.g., as described above, and instructions for how to use the devices in a procedure, such as a tissue structure modification procedure. In some embodiments, the kits can include a set of two or more implantable devices, e.g., three or more, four or more, five or more, six or more, etc. In some embodiments, a set of implantable devices includes two or more implantable devices in which at least two of the implantable devices have different relaxed lengths.

The kit can also include a deployment device, e.g., a minimally invasive deployment device, as described above. In some instances, the kit includes the implant preloaded on the deployment device, such that the kit includes a system made up of an implantable tissue structure modification device in a constrained state on the deployment device. In some instances, the kit includes a guide catheter, used to facilitate safe and directed access of the deployment device with preloaded implant from the access point (e.g. femoral artery puncture) through the vasculature and into the left ventricular chamber.

The kit can also include a measuring tool or guide to assist the clinician in selecting the appropriate length and/or size of the implantable device for implantation in a particular subject. The measuring tool or guide can be configured to assess an appropriate length based on direct measurements made in a subject, e.g., measurements obtained by measuring markings on a catheter positioned in a subject (e.g., radiopaque markings seen on fluoroscopy). The measuring tool or guide can also be used to obtain measurements from an imaging study (e.g., ultrasound, computed tomography, magnetic resonance imaging, etc) of a subject in a region of interest such as the right ventricle. In some instances, the kit also includes a guidewire, introducer sheath, syringes, and other accessories typically used in interventional cardiology procedures.

The instructions for using the devices as discussed above are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or sub-packaging) etc. In other embodiments, the instructions are present as an electronic storage data file present on a suitable computer readable storage medium, e.g., CD-ROM, diskette, etc. The instructions may take any form, including complete instructions for how to use the device or as a website address with which instructions posted on the world wide web may be accessed.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An implantable tissue structure modification device, the device comprising:
    a structure having first and second tissue securers separated by a contraction region that is structured to assume a linear constrained configuration when the device is in a constrained configuration and a curvilinear relaxed configuration when the device is in a relaxed configuration, wherein the device is configured to be implanted at a cardiac location and assume a first constrained arc length of the structure when the device is in the constrained configuration that is longer than a second relaxed arc length of the structure when the device is in the relaxed configuration; and
    wherein the device is configured so that the structure defines a shorter radius when present in the relaxed configuration as compared to the constrained configuration.

2. The device according to claim 1, wherein the device comprises a superelastic material.

3. The device according to claim 1, wherein the tissue securers are tines.

4. The device according to claim 1, wherein the tissue securers are hooks.

5. The device according to claim 1, wherein the device has an arced configuration when present in a relaxed state.

6. The device according to claim 1, wherein the device has a second moment of inertia to assume a desired orientation during delivery and implantation.

7. The device according to claim 1, wherein the device is configured to be associated in a constrained configuration with a minimally invasive deployment device.

8. The device according to claim 7, wherein the device comprises a passageway.

9. The device according to claim 8, wherein the passageway is associated with the first and second tissue securers.

10. The device according to claim 1, wherein the device comprises third and fourth tissue securers separated by the contraction region.

11. The device according to claim 10, wherein the device comprises fifth and sixth tissue securers associated with the contraction region.

12. The device according to claim 1, wherein the cardiac location is a ventricle wall location.

13. The device according to claim 12, wherein the ventricle wall location is a mitral valve ventricle wall location.

14. The device according to claim 1, wherein the first constrained length is at least about 20% longer than the second relaxed length.

15. A system comprising:
    (a) a minimally invasive deployment device; and
    (b) an implantable tissue structure modification device comprising a structure
    having first and second tissue securers separated by a contraction region that is
    structured to assume a linear constrained configuration when the device is in a constrained configuration and a curvilinear relaxed configuration when the device is in a relaxed configuration;
    wherein:
        the device is configured to be implanted at a cardiac location and assume a first constrained arc length of the structure when the device is in the constrained configuration that is longer than a second relaxed arc length of the structure when the device is in the relaxed configuration;
        the device is configured so that the structure defines a shorter radius when present in the relaxed configuration as compared to the constrained configuration; and
        the implantable device is associated in the constrained configuration with the minimally invasive deployment device.

16. The system according to claim 15, wherein the deployment device comprises a deployment wire that associates the implantable device to the deployment device in the first constrained configuration and wherein movement of the deployment wire dissociates the implantable device from the deployment device to assume the second relaxed configuration.

17. A kit comprising:
    (a) a minimally invasive deployment device; and
    (b) a first implantable tissue structure modification device, the implantable device comprising a structure having first and second tissue securers separated by a contraction region that is structured to assume a linear constrained configuration when the device is in a constrained configuration and a curvilinear relaxed configuration when the device is in a relaxed configuration;
    wherein
        the device is configured to be implanted at a cardiac location and assume a first constrained arc length of the structure when the device is in the constrained configuration that is longer than a second relaxed arc length of the structure when the device is in the relaxed configuration; and the device is configured so that the structure defines a shorter radius when present in the relaxed configuration as compared to the constrained configuration.

* * * * *